United States Patent

Denzel et al.

[11] 4,022,779
[45] May 10, 1977

[54] AMINO DERIVATIVES OF PYRIDO(3,4-b)PYRAZINE CARBOXYLIC ACIDS AND ESTERS

[75] Inventors: Theodor Denzel, Regensburg; Hans Hoehn, Tegernheim, both of Germany

[73] Assignee: E. R. Squibb & Sons, Inc., Princeton, N.J.

[22] Filed: Oct. 7, 1975

[21] Appl. No.: 620,469

Related U.S. Application Data

[63] Continuation-in-part of Ser. No. 491,884, July 25, 1974, abandoned.

[52] U.S. Cl. .................. 260/250 BC; 260/250 AH; 260/256.4 H; 260/268 BC; 424/250
[51] Int. Cl.$^2$ ................................ C07D 471/04
[58] Field of Search ............ 260/250 BC, 268 BC, 260/256.4 H, 250 A, 250 AH

*Primary Examiner*—Raymond V. Rush
*Assistant Examiner*—Jose Tovar

*Attorney, Agent, or Firm*—Lawrence S. Levinson; Merle J. Smith

[57] ABSTRACT

New derivatives of pyrido[3,4-b]pyridine carboxylic acids and esters and their acid addition salts have the general formula

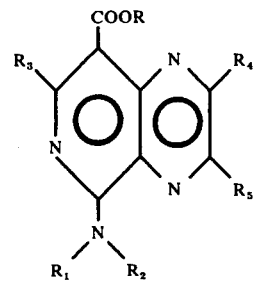

They are useful as anti-inflammatory agents and central nervous system depressants.

18 Claims, No Drawings

AMINO DERIVATIVES OF PYRIDO(3,4-b)PYRAZINE CARBOXYLIC ACIDS AND ESTERS

This application is a continuation-in-part of application Ser. No. 491,884, filed July 25, 1974, now abandoned.

SUMMARY OF THE INVENTION

The invention relates to the new amino derivatives of pyrido [3,4-b]pyrazine carboxylic acids and esters and acid addition salts thereof having the general formula:

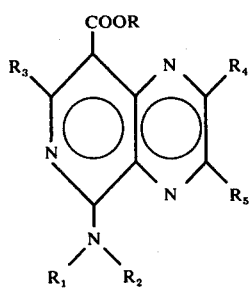

(I)

The symbols have the following meaning in formula I and throughout this specification:

The basic nitrogen group

is an acyclic amino moiety wherein $R_1$ and $R_2$ each is hydrogen, lower alkyl, lower alkanoyl, phenyl, substituted phenyl or di(lower alkylamino)lower alkyl, or forms a heterocyclic of 5 or 6 members in which an additional nitrogen is present, i.e., pyrrolidino, piperidino, dihydropyrimidinyl, dihydropyridazinyl or piperazino, each of which may bear as a substituent, a hydroxy-lower alkyl group, two lower alkyl groups or a phenyl ring, especially the piperidine and piperazine heterocyclics.

R, $R_3$, $R_4$ and $R_5$ each is hydrogen or lower alkyl.

The lower alkyl groups in any of the foregoing radicals include straight or branched chain hydrocarbon groups containing 1 to 7 carbon atoms. The lower alkanoyl groups are of the same type. Examples of the groups contemplated are methyl, ethyl, propyl, isopropyl, etc. Lower alkyl groups of 1 to 4 carbon atoms are preferred, especially the 1 and 2 carbon members of this group. The substituted phenyl groups include one or two simple substituents (preferably only one substituent, but they are the same groups if disubstituted), i.e., lower alkyl, lower alkoxy, halogen (F, Cl, Br or I, preferably Cl or Br), $CF_3$, amino or carboxy. Examples of the types of groups contemplated are o-, m- or p-chlorophenyl, o-, m- or p-tolyl 2,5-dichlorophenyl, 3,5-dimethylphenyl or 3,4-dimethoxyphenyl.

Preferred embodiments of this invention are as follows:

R is hydrogen, lower alkyl of 1 to 4 carbon atoms, especially ethyl.

$R_1$ and $R_2$ each is hydrogen, lower alkyl of 1 to 4 carbon atoms, especially butyl, N-(lower alkyl)-piperazino, especially N-methylpiperazino.

$R_3$ is lower alkyl especially methyl.

$R_4$ and $R_5$ each is hydrogen or lower alkyl, especially hydrogen and methyl.

DETAILED DESCRIPTION

The new compounds of formula I are formed by the following series of reactions. The symbols in the structural formulas have the same meaning as previously described.

A 4,6-dihydroxypyridine carboxylic acid ester of the formula

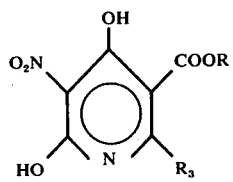

(II)

[produced analogous to the procedure described in Chem. Ber. 99, 244 (1966)] wherein R is lower alkyl is made to react with an inorganic acid chloride like phosphorus oxychloride, producing a compound of the formula:

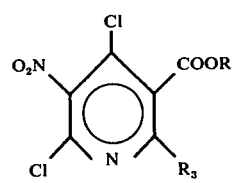

(III)

with two chlorine atoms in the 4- and 6- positions of the molecule. This compound is now treated with an amine like tert. butylamine in a solvent like alcohol in the presence of a base, e.g., an alkylamine like triethylamine, forming a compound of the formula:

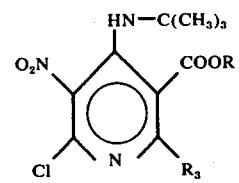

(IV)

Heating of this compound in an inert high boiling solvent like diphenylether, or without any solvent at a temperature of about 240°–260° C produces a compound of the formula:

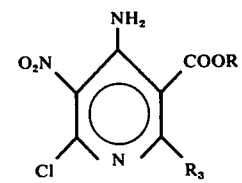

(V)

which is next treated with ammonia or the appropriate primary or secondary amine of the formula:

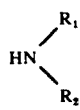

(VI)

in a solvent like alcohol in the presence of a base, e.g., an alkylamine like triethylamine. By this procedure a compound of the formula:

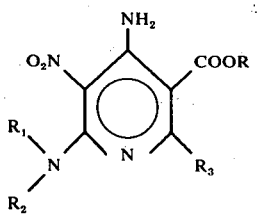 (VII)

is formed. The product is now hydrogenated either catalytically or with a metal-acid pair like zinc in acetic acid. This results in the formation of a compound of the formula:

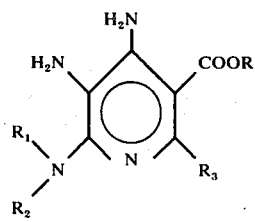 (VIII)

The compound of formula I is now produced by reacting the compound of formula VIII with an appropriate 1,2-diketone of the formula:

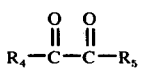 (IX)

The water formed by this reaction is removed by a water-separator using an aromatic solvent like benzene or toluene.

Compounds of formula VII wherein $R_1$ and $R_2$ are other than hydrogen can also be produced by an alternate process by reaction of a compound of formula III with an amine of formula VI (wherein $R_1$ and $R_2$ are not hydrogen) forming a compound of the formula

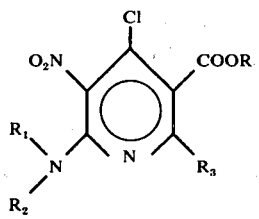 (X)

A product of formula VII is now produced by treatment of the compound of formula X with gaseous or aqueous ammonia in an autoclave in a solvent, e.g., an alcohol like ethanol.

The ester can be converted to the acid, i.e., wherein R is hydrogen, with a dilute alkali hydroxide like sodium hydroxide.

The bases of formula I form physiologically acceptable acid addition salts by reaction with an equivalent amount of the common inorganic and organic acids. Such salts include the hydrohalides, e.g., hydrobromide, hydrochloride, sulfate, nitrate, phosphate, acetate, citrate, oxalate, tartrate, maleate, succinate, benzoate, ascorbate, alkanesulfonate, e.g., methanesulfonate, arylsulfonate, e.g., benzenesulfonate, etc. It is frequently convenient to purify or isolate the product by forming an insoluble salt which is not necessarily physiologically acceptable. The base is then obtained by neutralization and another salt can then be formed by treatment with the appropriate inorganic and organic acid.

The new compounds of this invention have antiinflammatory properties and are useful, for example, to reduce local inflammatory conditions such as those of an edematous nature or resulting from proliferation of connective tissue in various mammalian species such as rats, dogs and the like when given orally in dosages of about 5 to 50 mg/kg/day, preferably 5 to 25 mg/kg/day, in single or 2 to 4 divided doses, as indicated by the carageenan edema assay in rats. The active substance can be utilized in compositions such as tablets, capsules, solutions or suspensions containing up to about 300 mg. per unit of dosage of a compound or mixture of compounds of formula I or physiologically acceptable acid addition salt thereof. They are compounded in conventional manner with a physiologically acceptable vehicle or carrier, excipient, binder, preservative, stabilizer, flavor, etc. as called for by accepted pharmaceutical practice. Topical preparations containing about 0.01 to 3 percent by weight of active substance in a lotion, salve or cream can also be used.

The compounds of this invention are also central nervous system depressants and can be used as tranquilizers or ataractic agents for the relief of anxiety and tension states, for example, in mice, cats, rats, dogs and other mammalian species. For this purpose a compound or mixture of compounds of formula I, or nontoxic, physiologically acceptable acid addition salt thereof, is administered orally or parenterally in a conventional dosage form such as tablet, capsule, injectable or the like. A single dose, or preferably 2 to 4 divided daily doses, provided on basis of about 1 to 50 mg. per kilogram per day, preferably about 2 to 15 mg. per kilogram per day, is appropriate. A conventional dosage in oral or parenteral form is compounded by incorporating about 10 to 250 mg. per unit of dosage with conventional vehicle, excipient, binder, preservative, stabilizer, flavor or the like as called for by accepted pharmaceutical practice.

The following examples constitute preferred embodiments and also illustrate how these and other members of the group are produced. Simple variation of the reactants and substitution in the reaction sequences described below readily yield other compounds within the scope of the invention. All temperatures are in degrees celsius.

EXAMPLE 1

7-Methyl-5-(4-methyl-1-piperazinyl)pyrido[3,4-b]pyrazine-8-carboxylic acid, ethyl ester a. 4,6-Dichloro-2-methyl-5-nitropyridine-3-carboxylic acid ethyl ester 242 g. of 4,6-dihydroxy-2-methyl-5-nitropyridine3-carboxylic acid ethyl ester (1 mol.) are heated at 120° with 500 ml. of phosphorus oxychloride for 3 hours. After this time, the excess phosphorus oxychloride is removed in vacuo and the black residue is decomposed by pouring into ice-water. About 1 liter of chloroform is added and the mixture is filtered to remove undissolved material. The organic layer is separated and the aqueous phase is extracted twice with 100 ml. portions of chloroform. The extract is dried over calcium chloride, filtered and evaporated to dryness. The resulting oil is crystallized with about 500 ml. of petroleum ether yielding 153 g. of 4,6-dichloro-2-methyl-5-nitropyridine-3-carboxylic acid ethyl ester (55%); m.p. 45°–46°.

b. 4-Chloro-2-methyl-6-(4-methyl-1-piperazinyl)-5-nitropyridine-3-carboxylic acid ethyl ester 55.8 g. of 4,6-dichloro-2-methyl-5-nitropyridine-3-carboxylic acid ethyl ester (0.2 mol.) are dissolved in 300 ml. of alcohol. After addition of 25 g. of triethylamine (0.25 mol.), the mixture is heated at reflux temperature and then 20 g. of N-methylpiperazine are dropped in with stirring. When the addition is completed, the temperature is maintained for 30 minutes. The solvent is distilled off, the residue is dissolved in benzene and the precipitated triethylammonium chloride filtered off. After evaporated of the solvent, the residual 4-chloro-2-methyl-6-(4-methyl-1-piperazinyl)-5-nitropyridine-3-carboxylic acid ethyl ester is recrystallized from methanol, yield 40 g. (60%), m.p. 59°–61°.

c. 4-Amino-2-methyl-6-(4-methyl-1-piperazinyl)-5-nitropyridine3-carboxylic acid ethyl ester 33.3 g. of 4-chloro-2-methyl-6-(4-methyl-1-piperazinyl)-5-nitropyridine-3-carboxylic acid ethyl ester (0.1 mol) are dissolved in about 100 ml. of alcohol. 50 ml. of aqueous ammonia solution (30%) are added and the mixture is heated in an autoclave at 80° for 10 hours. After this time, the solution is evaporated to dryness and the residue is extracted with hot alcohol. On cooling, 25.2 g. of 4-amino-2-methyl-6-(4-methyl-1-piperazinyl)-5-nitropyridine-3-carboxylic acid ethyl ester precipitate, (78%), m.p. 73°–75° (methanol).

d. 4,5-Diamino-2-methyl-6-(4-methyl-1-piperazinyl-pyridine-3-carboxylic acid ethyl ester 25.2 g. of 4-amino-2-methyl-6-(4-methyl-1-piperazinyl)-5-nitropyridine-3-carboxylic acid ethyl ester (0.078 mol.) are dissolved in 100 ml. of butyl alcohol and 0.5 g. of palladium on charcoal are added. The mixture is hydrogenated at 80° and a hydrogen pressure of 2 atoms. After 4 hours, the reaction is complete. The catalyst is filtered off and the solvent removed. The remaining oil comprising 4,5-diamino-2-methyl-6-(4-methyl-1-piperazinyl)pyridine-3-carboxylic acid ethyl ester is not purified further.

e. 7-Methyl-5-(4-methyl-1-piperazinyl)pyrido[3,4-b]pyrazine8-carboxylic acid ethyl ester 2.9g. of 4,5-diamino-2-methyl-6-(4-methyl)-1-piperazinyl)pyridine-3-carboxylic acid ethyl ester (0.01 mol.) are dissolved in 10 ml. of toluene and 1 g. of glyoxal monohydrate is added. The mixture is refluxed for 8 hours with stirring. The solvent is distilled off and the black residue is extracted with benzene after charcoal has been added. The benzene layer is evaporated and the residue distilled in vacuo. The 7-methyl-5-(4-methyl-1-piperazinyl)pyrido]3,4-b]pyrazine-8-carboxylic acid ethyl ester boils at 200° (0.05mm), yield 18 g. (56%).

f. 7-Methyl-5-(4-methyl-1-piperazinyl)pyrido[3,4-b]pyrazine-8-carboxlyic acid 10 gm. of 7-methyl-5-(4-methyl-1-piperazinyl)-pyrido[3,4-b]pyrazine-8-carboxylic acid ethyl ester are hydrolyzed with dilute sodium hydroxide solution to obtain 7-methyl-5-(4-methyl-1-piperazinyl)pyride[3,4-b]pyrazine-8-carboxylic acid.

EXAMPLE 2

7-Methyl-5-(1-piperidinyl)pyrido[3,4-b]pyrazine-8-carboxylic acid ethyl ester

By substituting piperidine for N-methylpiperazine in Example 1 b and the resulting 4-chloro-2-methyl-6-(1-piperidinyl)-5-nitropyridine-3-carboxylic acid ethyl ester is processed according to the procedure in Example 1 c-e, 7-methyl-5-(1-piperidinyl)pyrido[3,4-b]pyrazine-8-carboxlyic acid ethyl ester is obtained, m.p. 73°–74° (petroleum ether).

EXAMPLE 3

7-Methyl-5-(4-phenyl-1-piperazinyl)pyrido[3,4-b]pyrazine8-carboxylic acid ethyl ester By substituting N-phenylpiperazine for N-methylpiperazine in Example 1 b and the resulting 4-chloro-2-methyl-6-(4-phenyl-1-piperazinyl)-5-nitropyridine-3-carboxylic acid ethyl ester is processed as described in Example 1 c-e, 7-methyl-5-(4-phenyl-1piperazinyl)-pyrido[3,4-b]pyrazine-8-carboxylic acid ethyl ester is formed, m.p. 85°–87° (ligroin).

EXAMPLE 4

5-Butylamino-7-methylpyrido[3,4-b]pyrazine-8-carboxylic acid ethyl ester a. 6-Chloro-4[(1,1-dimethylethyl)amino]-2-methyl-5-nitropyridine-3-carboxylic acid ethyl ester 55.8 g. of 4,6-dichloro-2-methyl-5-nitropyridine-3-carboxylic acid ester (0.2 mol.) are dissolved in 300 ml. of alcohol and 25 g. of triethylamine. At reflux temperature, 14.6 g. of tert. butylamine are slowly added dropwise and the mixture is heated with stirring for an additional 30 minutes. The solvent is distilled off in vacuo and the residue is dissolved in benzene. The precipitated triethylamine hydrochloride is filtered off and the benzene layer is evaporated to dryness. The remaining oil, 6-chloro-4-[(1,1-dimethylethyl)amino]-2-methyl-5-nitropyridine-3-carboxylic acid ethyl ester crystallizes with methanol, yield 38.4 g. (61%), m.p. 40°–43°.

b. 4-Amino-6-chloro-2-methyl-5-nitropyridine-3-carboxylic acid ethyl ester 31.6 g. of 6-chloro-4[(1,1-dimethylethyl)amino]-2-methyl-5-nitropyridine-3-carboxylic acid ethyl ester (0.1 mol.) are heated with stirring at 250°–260° for 5 minutes. The dark oil is cooled to room temperature and 50 ml. of methyl alcohol are added. 18.2 g. of 4-amino-6-chloro-2-methyl-5-nitropyridine-3-carboxylic acid ethyl ester crystallize on cooling (70%), m.p. 89-91° (methanol).

c. 4-Amino-6-butylamino-2-methyl-5-nitropyridine-3-carboxylic acid ethyl ester 26 g. of 4-amino-6-chloro-2-methyl-5-nitropyridine-3-carboxylic acid ethyl ester (0.1 mol.) in 300 ml. of alcohol and 15 g. of triethylamine are treated with 7.3 g. of butylamine for 30 minutes at reflux temperature. After this time, the solution is evaporated to dryness and 100 ml. of ethyl acetate are added to the residue. The triethylammonium chloride is filtered off, the solvent is evaporated and the remaining oil recrystallized from methanol. The yield of 4-amino-6-butylamino-2-methyl-5-nitropyridine-3-carboxylic acid ethyl ester is 25 g. (84%), m.p. 74°–76° (methanol).

d. 4,5-Diamino-6-butylamino-2-methylpyridine-3-carboxylic acid ethyl ester.

6 g. of 4-Amino-6-butylamino-2-methyl-5-nitropyridine-3-carboxylic acid ethyl ester are hydrogenated in butyl alcohol with 0.1 g. of palladium on charcoal at 90° and 2 atoms. hydrogen pressure for 3 hours. The catalyst is filtered off, the butyl alcohol is removed and the residual 4,5-diamino-6-butylamino-2-methylpyridine-3-carboxylic acid ethyl ester is recrystallized from ethyl acetate, yield 5.0 g., m.p. 66°–68°.

e. 5-Butylamino-7-methylpyrido[3,4-b]pyrazine-8-carboxylic acid ethyl ester 2.6 g. of 4,5-diamino-6-butylamino-2-methylpyridine-3-carboxylic acid ethyl ester and 1 g. of gloxal monohydrate are refluxed for 5 hours in toluene with stirring. The mixture is evaporated to dryness and after addition of charcoal the residue is extracted with boiling ligroin. The charcoal is filtered off and the 5-n-butylamino-7-methylpyrido[3,4-b]pyrazine-8-carboxylic acid ethyl ester crystallizes on cooling, yield 1.9 g. (65%), m.p. 50°–52° (ligroin). Treatment of this product with one equivalent of dilute hydrochloric acid yields 5-butylamino-7-methylpyrido[3,4-b]pyrazine-8-carboxylic acid ethyl ester, hydrochloride. The toluenesulfonate is similarly obtained using toluenesulfonic acid.

EXAMPLE 5

5-(3-dimethylaminopropyl)amino-7-methylpyrido[3,4-b]pyrazine-8-carboxylic acid ethyl ester By substituting for butylamine in Example 4 (c) (3-dimethylamino)propylamine, 4-amino-6-(3-dimethylaminopropyl)amino-2-methyl-5-nitropyridine-3-carboxylic acid ethyl ester is obtained which is then processed as described in Example 4 (d) – (e). 5-(3-dimethylaminopropyl)amino-7-methylpyrido[3,4-b]pyrazine-8-carbboxylic acid ethyl ester is formed, m.p. 55°–57° (ligroin).

The hydrochloride salt is formed by treating the product with ethanolic HCl.

The following additional products are obtained by the procedure of Example 1.

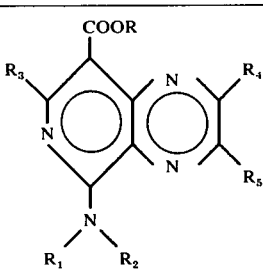

| Example | R | $\overset{R_1}{\underset{R_2}{N{<}}}$ | $R_3$ | $R_4$ | $R_5$ |
|---|---|---|---|---|---|
|  | H | —NH—$C_4H_9$ | $C_2H_5$ | H | H |
| 7 | $C_2H_5$ | —$NH_2$ | $CH_3$ | $CH_3$ | H |
| 8 | $C_2H_5$ | —NH—$C_2H_5$ | H | $CH_3$ | $CH_3$ |
| 9 | $C_2H_5$ | —NH—$C_3H_7$ | $CH_3$ | H | $CH_3$ |
| 10 | H | —NH—$C_4H_9$ | H | H | H |
| 11 | $C_2H_5$ | —$N(CH_3)_2$ | $CH_3$ | H | H |
| 12 | $C_2H_5$ | —$N(C_2H_5)_2$ | $C_2H_5$ | H | H |
| 13 | $C_2H_5$ | $NHCOCH_3$ | $CH_3$ | H | H |
| 14 | H | $N(COCH_3)_2$ | $CH_3$ | H | $CH_3$ |
| 15 | H | —NH—⟨phenyl⟩ | i-$C_3H_7$ | H | H |
| 16 | $C_2H_5$ | —NH—⟨phenyl-$CF_3$⟩ | H | $CH_3$ | $CH_3$ |
| 17 | H | —NH—⟨phenyl-COOH⟩ | $C_2H_5$ | H | H |
| 18 | $CH_3$ | —NH—⟨phenyl-$CH_3$⟩ | $C_2H_5$ | H | H |
| 19 | $C_2H_5$ | $N(C_6H_5)_2$ | $CH_3$ | H | H |
| 20 | $C_2H_5$ | NH—⟨2,4-di-$CH_3$-phenyl⟩ | $CH_3$ | H | H |
| 21 | $C_2H_5$ | NH—⟨2,4-di-$OCH_3$-phenyl⟩ | $CH_3$ | H | H |
| 22 | $C_2H_5$ | NH—⟨phenyl-Cl⟩ | H | H | H |

-continued

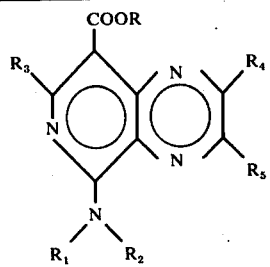

| Example | R | NR₁R₂ | $R_3$ | $R_4$ | $R_5$ |
|---|---|---|---|---|---|
| 23 | $CH_3$ | NH-(3,5-dibromophenyl) | $CH_3$ | H | H |
| 24 | H | -NH-C₆H₄-NH₂ | $CH_3$ | H | H |
| 25 | $C_3H_7$ | -NH-CH₂CH₂N(C₂H₅)₂ | $C_2H_5$ | $C_2H_5$ | H |
| 26 | $C_2H_5$ | -N(pyrrolidinyl) | $CH_3$ | H | H |
| 27 | $CH_3$ | -N(piperidinyl) | $C_2H_5$ | $CH_3$ | $CH_3$ |
| 28 | H | -N(4-(2-hydroxyethyl)homopiperazinyl) | H | H | H |
| 29 | $C_2H_5$ | NHCH₂CH₂N(CH₃)₂ | H | $CH_3$ | $CH_3$ |
| 30 | H | NHCH₃ | $CH_3$ | H | H |
| 31 | $C_2H_5$ | -N(pyrazolidinyl-NH) | $CH_3$ | H | H |
| 32 | $C_2H_5$ | -N(3,4-dimethylpiperidinyl) | $C_2H_5$ | H | H |
| 33 | $C_2H_5$ | -N(4-ethylpiperazinyl) | H | H | H |
| 34 | H | NH-(4-methylphenyl) | $CH_3$ | H | H |
| 35 | $C_2H_5$ | NH-C₆H₅ | $C_2H_5$ | H | H |
| 36 | H | NH(CH₂)₃N(C₂H₅)₂ | $C_2H_5$ | H | H |
| 37 | $C_2H_5$ | NHC₄H₉ | $CH_2CH_2CH(CH_3)_2$ | H | H |
| 38 | $C_2H_5$ | -N(pyrazinyl) | $CH_3$ | H | H |
| 39 | $C_2H_5$ | -N(3-methylpiperidinyl) | $CH_3$ | H | H |

-continued

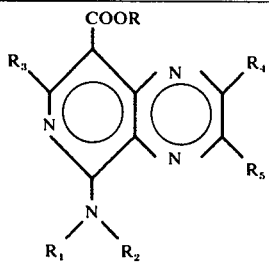

| Example | R | 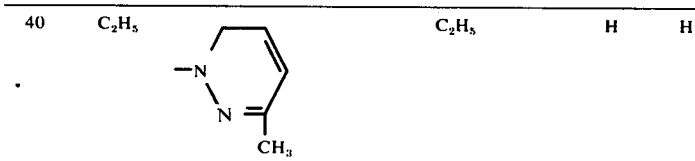(R₁,R₂) | R₃ | R₄ | R₅ |
|---|---|---|---|---|---|
| 40 | C₂H₅ | (pyridazinyl-CH₃ group) | C₂H₅ | H | H |

What is claimed is:

1. A compound of the formula

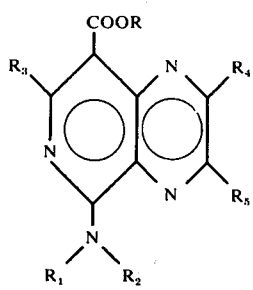

wherein R, $R_3$, $R_4$ and $R_5$ each is hydrogen or lower alkyl; $R_1$ and $R_2$ each is hydrogen, lower alkyl, lower alkanoyl, di(lower alkylamino)lower alkyl, phenyl, substituted phenyl, or

is an unsubstituted or substituted heterocyclic of the group consisting of pyrrolidino, piperidino, dihydropyrimidinyl, dihydropyridazinyl or piperazino; wherein the substituted phenyl bears one or two lower alkyl, lower alkoxy, halogen, trifluoromethyl, amino or carboxy groups, and the substituted heterocyclics bear a hydroxy-lower alkyl, one or two lower alkyl or a phenyl group; and acid addition salts thereof.

2. A compound as in claim 1 wherein R and $R_3$ each is lower alkyl and $R_4$ and $R_5$ each is hydrogen.

3. A compound as in claim 1 wherein R is ethyl, $R_3$ is methyl and $R_4$ and $R_5$ each is hydrogen.

4. A compound as in claim 1 wherein R is hydrogen or lower alkyl of 1 to 4 carbon atoms; $R_1$ and $R_2$ each is hydrogen, lower alkyl of 1 to 4 carbon atoms, or

N-(lower alkyl)piperazino; $R_3$ is lower alkyl and $R_4$ and $R_5$ each is hydrogen or lower alkyl.

5. A compound as in claim 2 wherein

is N-(lower alkyl)piperazinyl.

6. A compound as in claim 2 wherein

is 4-phenylpiperazinyl.

7. A compound as in claim 2 wherin $R_1$ is hydrogen and $R_2$ is lower alkyl.

8. A compound as in claim 2 wherein $R_1$ is hydrogen and $R_2$ is di(lower alkylamino)lower alkyl.

9. A compound as in claim 1 wherein R is ethyl, $R_4$ and $R_5$ each is hydrogen,

is 4-methyl-1-piperazinyl and $R_3$ is methyl.

10. A compound as in claim 1 wherein R is ethyl, $R_4$ and $R_5$ each is hydrogen,

is 4-phenyl-l-piperazinyl and $R_3$ is methyl.

11. A compound as in claim 1 wherein R is ethyl, $R_4$ and $R_5$ each is hydrogen,

is 4-phenyl-1-piperazinyl and $R_3$ is methyl.

12. A compound as in claim 1 wherein R is ethyl, $R_1$, $R_4$ and $R_5$ each is hydrogen, $R_2$ is butyl and $R_3$ is methyl.

13. A compound as in claim 1 wherein R is ethyl, $R_1$, $R_4$ and $R_5$ each is hydrogen, $R_2$ is 3-dimethylaminopropyl and $R_3$ is methyl.

14. A compound as in claim 1 wherein

is pyrrolidino.

15. A compound as in claim 1 wherein

is piperazino.

16. A compound as in claim 1 wherein

is piperidino.

is piperidino.

17. A compound of the formula

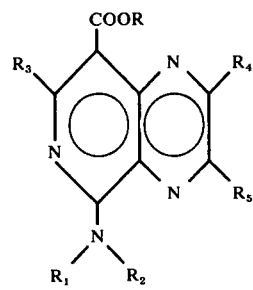

wherein R, $R_3$, $R_4$ and $R_5$ each is hydrogen or lower alkyl; $R_1$ and $R_2$ each is hydrogen, lower alkyl, lower alkanoyl, di(lower alkylamino)lower alkyl, phenyl, substituted phenyl, or

is an unsubstituted or substituted heterocyclic of the group consisting of pyrrolidino, piperidino, dihydropyrimidinyl, dihydropyridazinyl or piperazino; wherein the substituted phenyl bears one or two lower alkyl, lower alkoxy, halogen, trifluoromethyl, amino or carboxy groups, and the substituted heterocyclics bear a hydroxy-lower alkyl, one to two lower alkyl or a phenyl group.

18. A compound as in claim 1 wherein R, $R_3$, $R_4$ and $R_5$ each is hydrogen or lower alkyl; $R_1$ and $R_2$ each is hydrogen, lower alkyl, lower alkanoyl, di(lower alkylamino)lower alkyl, phenyl or substituted phenyl wherein the substituted phenyl bears one or two lower alkyl, lower alkoxy, halogen, trifluoromethyl, amino or carboxy groups, and acid addition salts thereof.

* * * * *

UNITED STATES PATENT AND TRADEMARK OFFICE
CERTIFICATE OF CORRECTION

PATENT NO. : 4,022,779
DATED : May 10, 1977
INVENTOR(S) : Theodor Denzel, Hans Hoehn It is certified that error appears in the above-identified patent and that said Letters Patent are hereby corrected as shown below:

Column 5, line 43, delete "atoms" and add --atmos.--
Column 5, line 67, delete "pyride" and add --pyrido--
Column 7, line 4, delete "atoms" and add --atmos.--
Column 8, line 14, delete "carbboxylic" and add --carboxylic--
Column 11, Claim 4, line 4 -- after the formula insert --is--

Signed and Sealed this

Fourth Day of October 1977

[SEAL]

Attest:

RUTH C. MASON
Attesting Officer

LUTRELLE F. PARKER
Acting Commissioner of Patents and Trademarks